United States Patent [19]

Schendell

[11] Patent Number: 5,511,975
[45] Date of Patent: Apr. 30, 1996

[54] CONNECTING MODULE FOR AN ORTHODONTIC TREATMENT MEANS

[76] Inventor: Claus Schendell, Gutenbergstrasse 9, D-82205 Gilching, Germany

[21] Appl. No.: 241,051

[22] Filed: May 10, 1994

[30] Foreign Application Priority Data

Nov. 28, 1993 [DE] Germany ............................ 9318121 U

[51] Int. Cl.⁶ .................................................. A61C 7/00
[52] U.S. Cl. .................................................. 433/5
[58] Field of Search ...................................... 433/5

[56] References Cited

U.S. PATENT DOCUMENTS

| | | | |
|---|---|---|---|
| 3,772,789 | 11/1973 | DeWeoskin | 433/5 |
| 4,121,341 | 10/1978 | DeWoskin | 433/5 |
| 4,215,983 | 8/1980 | Frazier | 433/5 |
| 4,368,039 | 1/1983 | Armstrong | 433/5 |
| 4,416,625 | 11/1983 | Armstrong | 433/5 |
| 4,553,934 | 11/1985 | Armstrong et al. | 433/5 |
| 4,704,086 | 11/1987 | Armstrong et al. | 433/5 |
| 4,872,836 | 10/1989 | Grove | 433/5 |

*Primary Examiner*—Cary E. O'Connor
*Attorney, Agent, or Firm*—Rosen Dainow & Jacobs

[57] ABSTRACT

Connecting module for an orthodontic treatment device, consisting of a flat housing with a bow resiliently latched thereto for the attachment to a head harness and a flat fastening band for the attachment to a face bow, the one end of which comprising a flat slide bar section, projecting through an opening in the housing into same, and being held there by means of a helical pressure spring which is located between the free end of the bar slide section and an abutment in the housing, the outer diameter of the helical pressure spring being larger than the thickness of the slide bar section, which may be partially pulled out of the housing against the bias of the helical pressure spring. The slide bar section has an opening extending in the longitudinal direction thereof, with the helical pressure spring being disposed between the axial ends thereof.

17 Claims, 1 Drawing Sheet

CONNECTING MODULE FOR AN ORTHODONTIC TREATMENT MEANS

The present invention relates to a connecting module for an orthodontic treatment means, consisting of a flat housing with a bow resiliently locked thereto for being attached to a head harness and of a flat fastening band for being attached to a face bow, the one end of which comprising a flat slide bar section, which projects through an opening in the housing into the same, and which is there held by means of a helical pressure spring clamped between the free end of the slide bar section and a carrier in the housing, the outer diameter of said spring being larger than the thickness of the slide bar section, which may be pulled partially out of the housing against the bias of the helical pressure spring. Such a connecting module is known from U.S. Pat. No. 4,226,589. Two of these connecting modules each are used at an orthodontic treatment means for distalization of e.g. the upper 6-years molars as a resilient connection between the head harness and the face bow. The bows of the connecting modules are attached to the head harness, whereas the flat fastening bands are provided with a plurality of holes for the variable attachment of the face bow by hooking. A pressure force may be generated by means of the helical pressure springs between the neck of the patient, serving as hypomochlion and the molars at which a pressure bow affixed to the face bow is anchored, said pressure force resulting in a distalization of the molars.

The treatment means can be opened by means of the resiliently locked attachment of the bows at the housings of the connecting modules, in order to remove it by the patient. At the same time, this resilient lock connection between the bow and the housing serves safety purposes, since this connection will be released in case of overload.

In the known connecting module, the flat fastening band consists of a soft, easily bendable plastic material. The flat fastening band is connected to the slide bar section as a one-part unit. The spring forces, which are used in the treatment elements of the aforementioned kind in order to achieve the distalization of the molars, are rather strong, which requires the flat slide bar section, which is surrounded in the known connecting module by the helical pressure spring, to have a predetermined minimum width in order not to break or suffer from fatigue. In the commercially available embodiments, which are provided with the features of the aforementioned U.S. Pat. No. 4,226,589, this width is 6 mm, which results in an outer diameter of the helical pressure spring of approximately 7 mm, which finally leads to a housing thickness of approximately 11 mm. This is very annoying for the patient, since the orthodontic treatment means is in particular carried during the night, because the connecting module pushes against the temples or against the cheeks of the patient.

A further disadvantage of the known connecting module is that the bow for being attached to the head harness consists of plastic material. This material changes its spring properties by temperature, and the spring force thereof decreases by frequent use, and fatigue then leads to rupture. Furthermore, a bow made of plastic material does not enable to adjust the support force individually. A very lively patient requires a stronger support force at the connecting module than a comparable calm patient. Greater support forces are required in particular during sport activities, so that the orthodontic means does not open by itself. On the other hand, the flexible lock connection between the bow and the housing has to be very reliable in order to fulfill a safety function if too heavy forces are acting on the orthodontic treatment means, for example if the patient got caught therewith somewhere.

It is the object of the invention to provide a connecting module of the aforementioned kind, which is more comfortable to wear by the patient.

According to the invention, this object is attained in that the slide bar section has an opening extending in the longitudinal direction thereof, with the helical pressure spring being disposed between the axial ends thereof.

This construction enables to severely reduce the diameter of the helical pressure springs which determines the thickness of the connecting module to a large extent. The tensile forces, which are necessary in accordance with the treatment and which are to be transmitted by the slide bar section, are received by the two webs which laterally limit said opening.

It is favourable for an improved guide of the slide bar section in the housing, if this housing has an elongated flat chamber, open at one end of the housing and the webs of the slide bar section being guided between the walls thereof, with an axially extending, central chamber of circular cross-section, which—seen in cross-section—is situated in the center of the flat chamber, and which receives the helical pressure spring and is partially closed against said one end of the housing by an abutment, at which the helical pressure spring is supported.

For the installation, when assembling the connecting module, it is favourable if a projection is provided at the axial ends of the opening, said projection projecting axially into the opening and being enclosed by the helical pressure spring. These projections hold the helical pressure spring at the flat slide bar section, before the insertion of the componentry consisting of fastening band and helical pressure spring. The projections may possibly be elongated so that the free ends thereof are opposing one another at a small spacing of approximately 2 to 5 mm to one another. The helical pressure spring is then fixedly held by the projections. One of the projections should have a relatively short length of approximately only 2 to 5 mm to enable an easy mounting of the helical pressure spring.

According to an especially advantageous embodiment of the invention, the bow, which is determined for fixing the connecting module to the head harness, consists of a flexible wire, and it has a preferably horse shoe-like bent section, which is latchingly disposed in a groove at the housing circumference. A bow of this kind enables by bending at the legs thereof to individually adjust the support force of the same at the housing. Moreover, the spring properties of a wire material, e.g. consisting of special steel are completely constant in the scale of normal ambient temperature, and such a wire material is basically free of fatigue and does not break so that disadvantages of the known plastic bow are completely unknown for such a bow.

The housing advantageously consists of two identical housing shells, preferably made of plastic material, which are adhered or welded together or latched or connected in another fashion.

The thickness of the housing can be reduced by means of the invention to approximately 8 mm by means of dimensions of the flat fastening band and comparable spring forces comparable to the known example.

The invention will now be described under reference to the drawings.

Figure 1:
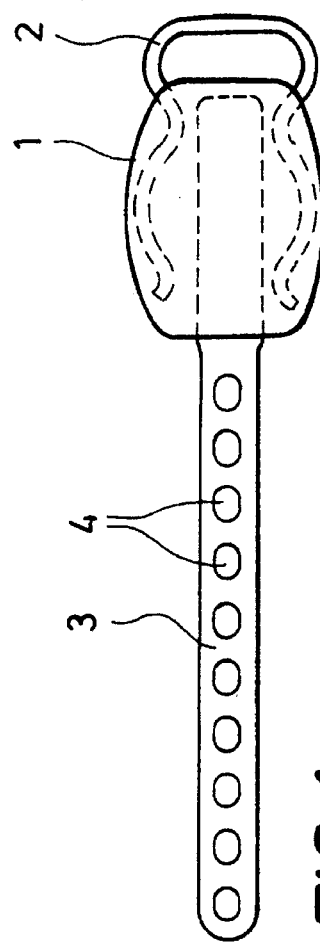
FIG. 1 is a side view of a connecting module according to the invention.

The connecting module according to FIG. 1 consists of a flat housing 1 with a rounded-off circumference, a wire bow 2 resiliently latched thereto, and a flat fastening band 3 displaceably mounted in the housing, said fastening band comprising a plurality of holes 4, at which a face bow (not shown) can be hooked.

Figure 2:
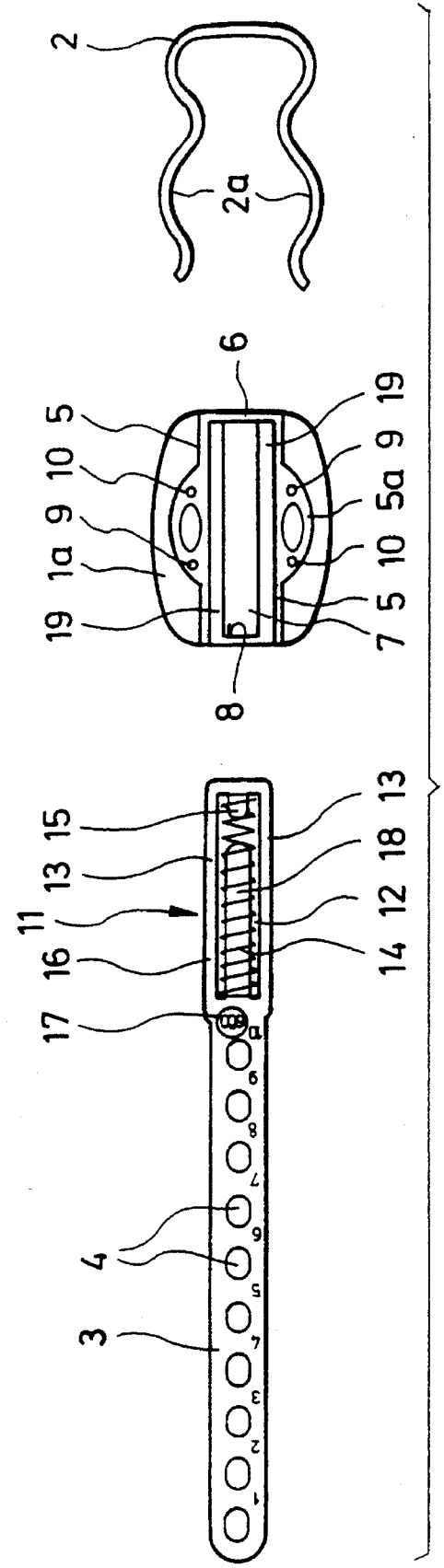
FIG. 2 is an explosion drawing of the connecting module according to FIG. 1 when the housing is opened.

Only one shell 1a of the housing 1 consisting of two shells is shown in FIG. 2 in opened condition. A flat chamber can be seen in the housing, said chamber being limited by lateral walls 5 and a rear end wall 6. Said flat chamber is open at the end opposite the end wall 6. An elongated central chamber 7 of circular cross-section is located in the center of the flat chamber, from which of course only one half is shown in FIG. 7. The central chamber 7 extends from the rear end wall 6 up to a front abutment 8 at the opposite end of the housing 1. The two housing shells can be aligned with respect to one another and combined to form a housing 1 by the aid of pins 9, which fit into holes 10 of the opposite housing shell, possibly by an additional adhering, welding or clamping process.

The flat fastening band 3 can furthermore be seen in FIG. 2, which on one end goes over into the slide bar section 11, which has a longitudinal opening 12 extending in the axial direction. The break-out is laterally limited by webs 13, and a helical pressure spring 14 is disposed between these webs, said helical pressure spring more or less loosely contacting the two ends of the opening 12. Projections 15 and 16 project at the slide bar section 11 from the axial ends of the opening 12. In the shown example which shows the connecting module in real dimension, the projection 15 is approximately 4 mm long, whereas the projection 16 is approximately 23 mm long and the projections 15 and 16 are opposing one another at a spacing of approximately 3 mm. In this manner, the helical pressure spring 14 can be very easily installed and secured in its position.

The holes 4 are indicated with numbers, which are an orientation aid for the patient when hooking in the face bow. A marking 17 is situated at the fastening band 3, which contains a symbol (inscription) for the spring force of the connecting module, which is to be exerted by same. In the present case, "600" represents a spring force of 600 g. This spring force occurs if when partially pulling the slide bar section 11 out of the housing 1, a marking 18 disposed at the projection 16 appears at the housing periphery.

For installation, only the pre-mounted flat fastening band 3 with helical pressure spring 14 positioned there has to be inserted into a housing shell 1a. In the shown example, the opening 12 has a length, which is slightly shorter than the length of the central chamber 7, so that the slide bar section 11 may be inserted into the housing shell together with the helical pressure spring 14 completely without any tensions. Then, only the second, equal housing shell must be mounted and adhered to, or welded or connected in any other way, to the first housing shell. Finally, the wire bow 2 is snapped open. The walls 5 at the housing 1 each comprise a bow-shaped section 5a in order for the snap effect to develop, and the wire bow 2 has an approximately horse shoe shaped section 2a matching therewith.

During application, the webs 13 of the slide bar section 11 are safely guided by flat wall sections 19 of the flat chamber located adjacent the central chamber 7 as well as the lateral walls 5 thereof. When the slide bar section 11 is pulled out of the housing, the end of the helical pressure spring 14 facing the flat fastening band 3 is supported at the carrier 8, whereas the other end of the helical pressure spring is supported at the rear end of the slide bar section 11 at the root of the projection 15. The helical pressure spring 14 is thus compressed during extraction of the slide bar section 11.

The appearance of the marking 18 outside the housing indicates that the set force of 600 g in the shown example is reached.

The further details of the orthodontic treatment means, i.e. the head harness and the face bow, are irrelevant in the present case, since these members are known to the person skilled in the art and since the invention does not refer thereto.

I claim:

1. Connecting module for an orthodontic treatment means, consisting of a flat housing with a bow resiliently latched thereto for the attachment to a head harness and a flat fastening band for the attachment to a face bow, said fastening band comprising a flat slide bar section at one end, projecting through an opening in the housing into same, and being held there by means of a helical pressure spring which is located between the free end of the slide bar section and an abutment in the housing, said helical pressure spring having an outer diameter which is larger than a thickness of the slide bar section, which may be partially pulled out of the housing against a bias of the helical pressure spring, said slide bar section having an opening extending in a longitudinal direction of said slide bar section and having axial ends, with the helical pressure spring being disposed between said axial ends.

2. Connecting module according to claim 1, wherein an elongated flat chamber is formed in the housing, said chamber being open at one end of the housing and with the slide bar section being guided between walls of said flat chamber, and an axially extending central chamber of a circular cross-section being provided in a center of the flat chamber, seen in cross-section, the helical pressure spring being disposed within said central chamber, said central chamber being partially closed against said one end of the housing by an abutment, at which the helical pressure spring is supported.

3. Connecting module according to one of claims 1 and 2, wherein a projection is formed at each axial end of the opening, said projections axially projecting into the opening and being surrounded by the helical pressure spring.

4. Connecting module according to claim 3, wherein the bow consists of a flexible wire and the housing consists of two identical housing shells fixedly connected to one another, and that a circumferential groove is provided in a separation line of the housing shells, into which the wire bow is latched.

5. Connecting module according to claim 2, wherein the projections have free ends which have a mutual spacing of approximately 2 to 5 mm to one another.

6. Connecting module according to claim 5, wherein the bow consists of a flexible wire and the housing consists of two identical housing shells fixedly connected to one another, and that a circumferential groove is provided in a separation line of the housing shells, into which the wire bow is latched.

7. Connecting module according to claim 5 wherein at least one of the projections has a length of approximately 2 to 5 mm.

8. Connecting module according to claim 3, wherein at least one of the projections has a length of approximately 2 to 5 mm.

9. Connecting module according to one of claims 1 and 2, wherein the bow consists of a flexible wire and the housing consists of two identical housing shells fixedly connected to one another, and that a circumferential groove is provided in a separation line of the housing shells, into which the wire bow is latched.

10. Connecting module according to claim 9, characterized in that the wire bow comprises a horse shoe-like section and the housing has wall sections complementary thereto.

11. A module for resiliently connecting a face bow to a head harness in an orthodontic treatment device comprising:

a fastening band releasably attachable at one end to the face bow and having a slide bar section at another end, the slide bar section having a longitudinally extending opening therein;

a bow releasably attachable to the head harness;

a housing resiliently latchable to the bow and having a hole into which the slide bar section projects; and pressure means for resiliently holding the slide bar section in the housing such that the slide bar section may be partially pulled out of the housing, the pressure means being disposed within the opening in the slide bar section and being supported when longitudinal force is applied between the housing and the fastening band by an axial end of the opening in the slide bar section and by support means in the housing.

12. The module according to claim 11 wherein the pressure means is a helical pressure spring.

13. The module according to claim 12 wherein the helical pressure spring has an outer diameter which is larger than a thickness of the slide bar section.

14. The module according to claim 12 wherein the opening in the slide bar section has two axial ends and at least one projection is formed at at least one of the axial ends which extends axially into the opening and is surrounded by at least part of the helical pressure spring.

15. The module according to claim 11 wherein the housing and slide bar section are substantially flat.

16. A connecting module for an orthodontic treatment device having a face bow and head harness comprising:

a fastening element releasably attachable at one end to the face bow and having a sliding section at another end;

a housing element having a hole into which the sliding section projects;

means for releasably attaching the head harness to the housing element; and compression spring means for resiliently holding the sliding section in the housing element such that the sliding section may be partially pulled out of the housing element by an application of force to the housing element or fastening element, the interior of the compression spring means being at least partially vacant in the axial direction thereof.

17. A connecting module for an orthodontic treatment device having a face bow and head harness comprising:

a fastening element releasably attachable to the face bow and having engaging means for engaging a compression spring;

a housing having a hole into which the engaging means projects and having support means for supporting a compression spring;

means for releasably attaching the head harness to the housing; and a compression spring which resiliently holds the fastening element to the housing against an application of force to the fastening element or housing, the compression spring being engaged at one end by the engaging means and supported at the other end by the support means during the application of such force;

wherein the engaging means extends along the exterior of the compression spring.

* * * * *